United States Patent
Belanger

(10) Patent No.: US 7,265,662 B2
(45) Date of Patent: Sep. 4, 2007

(54) APPARATUS AND METHOD FOR INSPECTING CONTAINERS

(75) Inventor: Paul Belanger, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 201 days.

(21) Appl. No.: 11/081,649

(22) Filed: Mar. 17, 2005

(65) Prior Publication Data

US 2006/0221877 A1   Oct. 5, 2006

(51) Int. Cl.
*G08B 19/00* (2006.01)

(52) U.S. Cl. ............... 340/521; 340/426.2; 340/426.25; 340/619; 340/626; 340/632; 382/142; 382/108; 382/149

(58) Field of Classification Search ............... 340/521, 340/426.2, 426.25, 619, 626, 632; 382/142, 382/108, 149
See application file for complete search history.

(56) References Cited

U.S. PATENT DOCUMENTS

| | | | |
|---|---|---|---|
| 5,012,117 A | 4/1991 | Karafa et al. ............... | 250/572 |
| 5,095,204 A | 3/1992 | Novini ................... | 250/223 B |
| 5,812,693 A | 9/1998 | Burt et al. .................. | 382/149 |
| 6,385,558 B1* | 5/2002 | Schlemm .................... | 702/182 |
| 6,411,905 B1 | 6/2002 | Guoliang et al. ............. | 702/23 |
| 6,531,707 B1 | 3/2003 | Favreau et al. ......... | 250/559.46 |
| 6,620,109 B2 | 9/2003 | Hanson, III .................. | 600/532 |
| 6,748,104 B1 | 6/2004 | Bachelder et al. .......... | 382/151 |
| 6,773,398 B2 | 8/2004 | Ogasawara et al. ......... | 600/437 |
| 6,790,183 B2 | 9/2004 | Murphy ....................... | 600/532 |
| 6,856,251 B1 | 2/2005 | Tietsworth et al. ......... | 340/626 |
| 6,894,775 B1* | 5/2005 | Cech ....................... | 356/239.1 |
| 6,993,176 B2* | 1/2006 | Yamagishi et al. ......... | 382/142 |
| 2003/0012435 A1 | 1/2003 | Forde .......................... | 382/167 |
| 2004/0194980 A1 | 10/2004 | McSheffrey, Jr. et al. .... | 169/75 |
| 2004/0197012 A1 | 10/2004 | Bourg, Jr. et al. .......... | 382/110 |

FOREIGN PATENT DOCUMENTS

GB   2263777   4/1993

OTHER PUBLICATIONS

Bharati, M.H. and MacGregor, J.F., "Multivariate Image Analysis for Real-Time Process Monitoring and Control", *Industrial and Engineering Chemistry Research* pp. 4715-4724, vol. 37, 1998.
Champagne, M., and Dudzic, M., "Industrial Use of Multivariate Statistical Analysis for Process Monitoring and Control", *Proceedings of the American Control Conference*, May 2002.
Champagne, M. and Ivanov, I., "Multigrade Modelling—Paperboard Quality Modeling", *Proceedings of the American Control Conference*, May 2002.

* cited by examiner

*Primary Examiner*—Tai Nguyen
(74) *Attorney, Agent, or Firm*—Gerald L. Coon

(57) ABSTRACT

This invention relates to an integrated apparatus and method for inspection of a container adapted to hold a pressurized gas. The integrated apparatus comprises (i) an imaging device configured to obtain image data corresponding to the container and to transmit the image data to a central station, (ii) a sound detecting device configured to obtain acoustic data corresponding to the container and to transmit the acoustic data to the central station, (iii) optionally an odor detecting device configured to obtain odor data corresponding to the container contents and to transmit the odor data to the central station, (iv) wired or wireless electronic circuits in communication between each device and the central station for transmitting signals, the signals including the data, to the central station, and (v) the central station configured to receive the data transmitted by each device.

18 Claims, 2 Drawing Sheets

APPARATUS AND METHOD FOR INSPECTING CONTAINERS

FIELD OF THE INVENTION

This invention relates to an apparatus and method for inspecting containers adapted to hold a pressurized gas.

BACKGROUND OF THE INVENTION

A large number of cylinders are filled each year with gases of various kinds and properties. Before each cylinder is filled, certain pre-fill inspections must be completed. The inspections should include at least a visual inspection to locate gouges, dents, burn marks, and discoloration, a sniff test to identify possible contaminants, a dead ring test to gauge the structural integrity of the cylinder, and a liquid check to detect the accumulation of liquids within the cylinder.

U.S. Patent Application Publication 2004/0194980 A1 discloses an apparatus for remote inspection of fluid containers having an electronic circuit in communication between each container and a remote central station. The electronic circuit is adapted to issue a wireless signal to the remote central station upon detection of pre-determined internal conditions, such as an out-of-range pressure condition of fluid contained within the volume of the container, or upon detection of predetermined external conditions, such as the lack of presence of the container in its installed position or the presence of an obstruction to viewing of or access to the container.

All industrial gas suppliers have pre-fill inspections that are performed prior to the filling of a cylinder. These pre-fill inspections are typically performed manually and therefore are time consuming and are often error-prone since they require subjective judgment. It would be desirable to reduce the time required to perform the pre-fill cylinder inspections thereby resulting in considerable cost savings.

It would also be desirable to identify with high reliability cylinders that are structurally unfit to be filled with high pressure gas. The structural integrity of all cylinders degrades over time with use, so reliably detecting the cylinders that are unfit to be filled can avoid a cylinder bursting, which could result in injury or death. In addition to natural degradation, an ongoing problem is that of human tampering with cylinders. One problem in packaged gas operations is the appearance of cylinders that have been altered to facilitate the drug trade. For example, on occasion cylinders have been found that were cut open and the porous mass removed so that the cylinder could be used to transport drugs. There has also been a recent surfacing of cylinders that have been tampered with for other purposes.

Removing the cylinder inspection errors that result from the subjective judgment of an operator/inspector can have a positive impact on operator/inspector safety because more defects are likely to be identified. It would be desirable to provide an apparatus and method for quickly and accurately determining if a cylinder is fit to remain in service. It would further be desirable to provide information to an operator/inspector that will help point out the type of defect, its location, and its severity.

SUMMARY OF THE INVENTION

This invention relates to an apparatus and method for remote inspection of industrial gas containers, e.g., cylinders or tanks. The containers can be distributed, for example, throughout a storage site, factory or other industrial facility.

In particular, this invention relates to an integrated apparatus for inspection of a container adapted to hold a pressurized gas, the integrated apparatus comprising (i) an imaging device configured to obtain image data corresponding to the container and to transmit the image data to a central station, (ii) an electronic circuit in communication between the imaging device and the central station for transmitting a signal, the signal including image data, to the central station, (iii) a sound detecting device configured to obtain acoustic data corresponding to the container and to transmit the acoustic data to the central station, (iv) an electronic circuit in communication between the sound detecting device and the central station for transmitting a signal, the signal including acoustic data, to the central station, (v) optionally an odor detecting device configured to obtain odor data corresponding to the container contents and to transmit the odor data to the central station, (vi) optionally an electronic circuit in communication between the odor detecting device and the central station for transmitting a signal, the signal including odor data, to the central station, and (vii) the central station configured to receive image data transmitted by the imaging device, acoustic data transmitted by the sound detecting device and odor data transmitted by the odor detecting device.

This invention also relates to an integrated inspection method of a container adapted to hold pressurized gas, the method comprising (i) positioning the container for inspection, (ii) obtaining image data corresponding to the container using an imaging device configured to transmit the image data to a central station, (iii) transmitting a signal including image data to the central station by an electronic circuit in communication between the imaging device and the central station, (iv) processing the image data to detect defects in the container, (v) obtaining acoustic data corresponding to the container using a sound detecting device configured to transmit the acoustic data to the central station, (vi) transmitting a signal including acoustic data to the central station by an electronic circuit in communication between the sound detecting device and the central station, (vii) processing the acoustic data to detect defects in the container and/or the presence of liquids in the container, (viii) optionally obtaining odor data corresponding to the container contents using an odor detecting device configured to transmit the odor data to the central station, (ix) optionally transmitting a signal including odor data to the central station by an electronic circuit in communication between the odor detecting device and the central station, and (x) optionally processing the odor data to identify the container contents.

An important advantage that this invention has over the prior art is that it integrates or combines several types of diagnostic signals to determine the structural integrity of a gas cylinder. The optical and acoustic testing provide complimentary information for a much more reliable and thorough test. An economic advantage of this invention is the availability of inexpensive sensors in the form of digital cameras and microphones.

An added advantage is the simplicity of the methods proposed. There is no need for special sources of illumination, light scattering devices, speed controls for rotation of the object being inspected. The sensors are readily available in the retail market. There is no need for transducers designed to impart a specific frequency sound wave into the metal. There is also no need to rotate the sensors or the cylinder in order to provide the diagnostic information being sought.

DETAILED DESCRIPTION OF THE INVENTION

Figure 1:
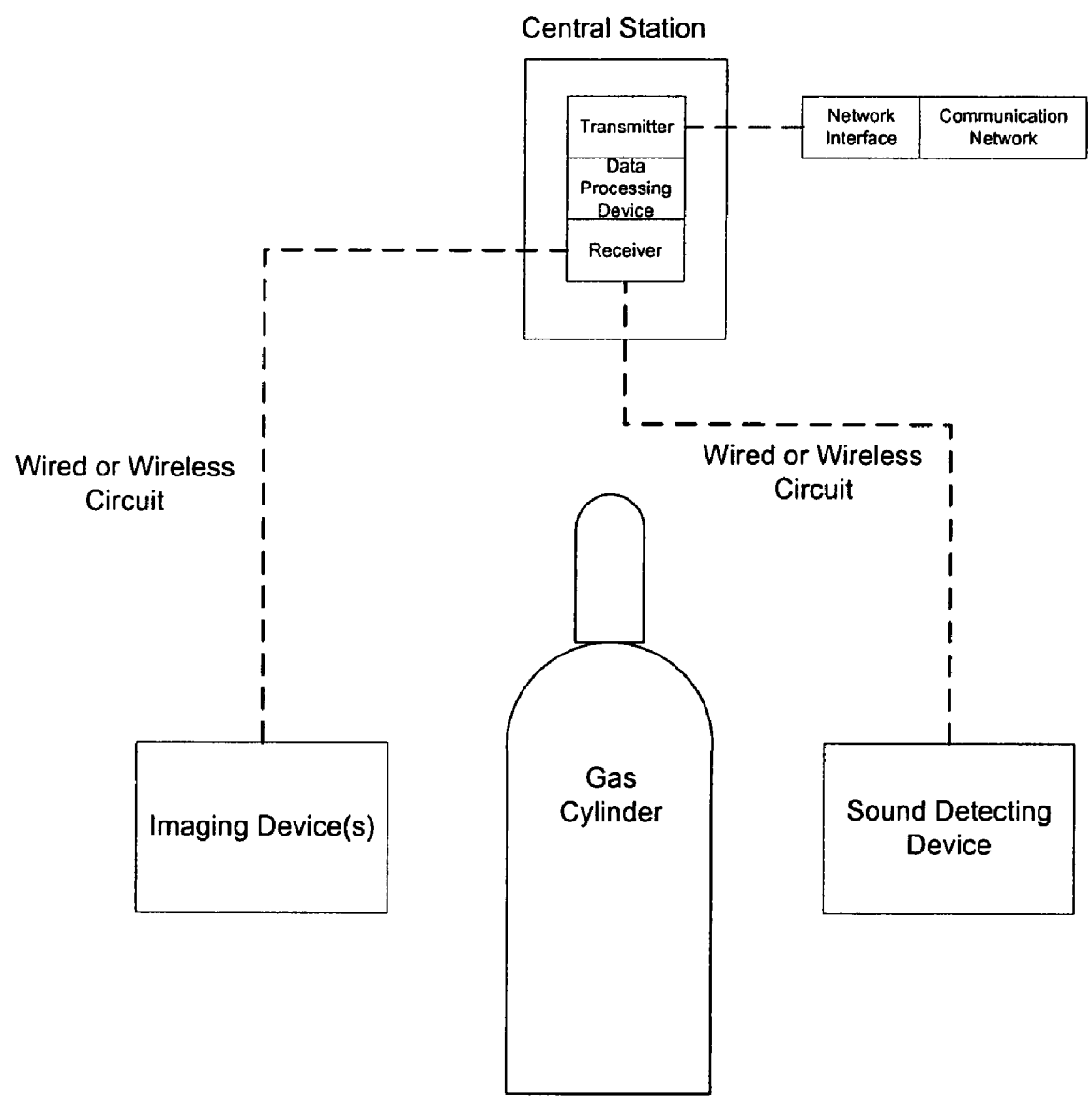
FIG. 1 depicts an illustrative apparatus or system of this invention for inspection of a gas cylinder, the apparatus or system comprising a central station, imaging device(s), an electronic circuit, e.g., wired or wireless, in communication between the imaging device(s) and the central station, a sound detecting device, and an electronic circuit, e.g., wired or wireless, in communication between the sound detecting device and the central station.
Figure 2:
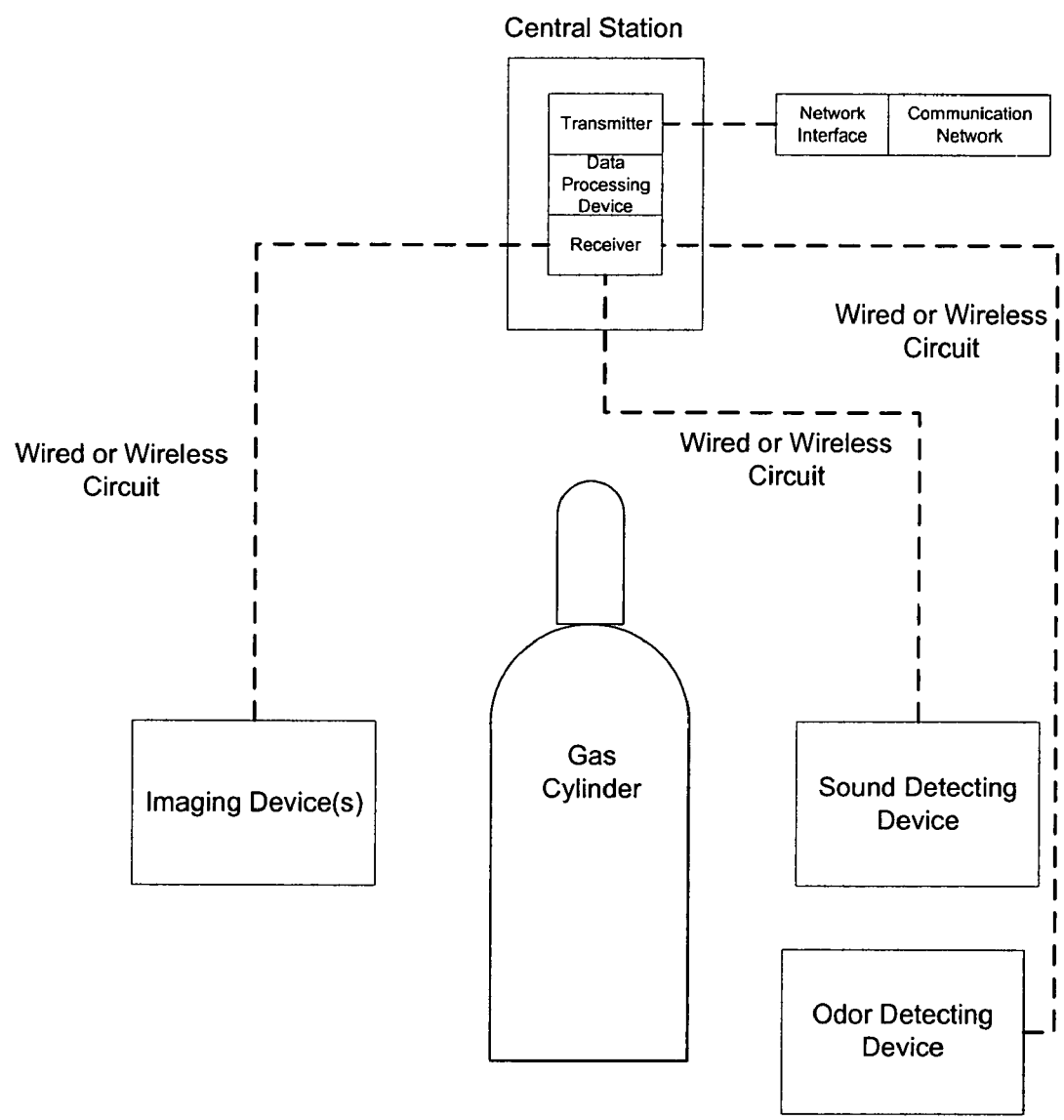
FIG. 2 depicts an illustrative apparatus or system of this invention for inspection of a gas cylinder, the apparatus or system comprising a central station, imaging device(s), an electronic circuit, e.g., wired or wireless, in communication between the imaging device(s) and the central station, a sound detecting device, an electronic circuit, e.g., wired or wireless, in communication between the sound detecting device and the central station, an odor detecting device, and an electronic circuit, e.g., wired or wireless, in communication between the odor detecting device and the central station.

As indicated above, this invention relates to an integrated apparatus for inspection of a container adapted to hold a pressurized gas, the integrated apparatus comprising (i) an imaging device configured to obtain image data corresponding to the container and to transmit the image data to a central station, (ii) an electronic circuit in communication between the imaging device and the central station for transmitting a signal, the signal including image data, to the central station, (iii) a sound detecting device configured to obtain acoustic data corresponding to the container and to transmit the acoustic data to the central station, (iv) an electronic circuit in communication between the sound detecting device and the central station for transmitting a signal, the signal including acoustic data, to the central station, (v) optionally an odor detecting device configured to obtain odor data corresponding to the container contents and to transmit the odor data to the central station, (vi) optionally an electronic circuit in communication between the odor detecting device and the central station for transmitting a signal, the signal including odor data, to the central station, and (vii) the central station configured to receive image data transmitted by the imaging device, acoustic data transmitted by the sound detecting device and odor data transmitted by the odor detecting device.

Also, as indicated above, this invention relates to an integrated inspection method of a container adapted to hold pressurized gas, the method comprising (i) positioning the container for inspection, (ii) obtaining image data corresponding to the container using an imaging device configured to transmit the image data to a central station, (iii) transmitting a signal including image data to the central station by an electronic circuit in communication between the imaging device and the central station, (iv) processing the image data to detect defects in the container, (v) obtaining acoustic data corresponding to the container using a sound detecting device configured to transmit the acoustic data to the central station, (vi) transmitting a signal including acoustic data to the central station by an electronic circuit in communication between the sound detecting device and the central station, (vii) processing the acoustic data to detect defects in the container and/or the presence of liquids in the container, (viii) optionally obtaining odor data corresponding to the container contents using an odor detecting device configured to transmit the odor data to the central station, (ix) optionally transmitting a signal including odor data to the central station by an electronic circuit in communication between the odor detecting device and the central station, and (x) optionally processing the odor data to identify the container contents.

As used herein, pressurized gas includes a gas that is stored at a pressure equal to, less than, or greater than its critical pressure. Illustrative pressurized gases include, but are not limited to, nitrogen, oxygen, argon, helium, carbon dioxide, hydrogen, medical gases, semiconductor process gases, specialty gases, welding and cutting gases, and the like.

For the imaging or visual analysis inspection of containers, this invention may employ one or more cameras, e.g., digital cameras, mounted where pictures could be taken of a cylinder. If only one camera is mounted, then the cylinder may be rotated by a device in the floor while the camera takes pictures of the cylinder from different angles. If several cameras are used, then the picture taking can be done without rotating the cylinder. The images from the cameras would then be transmitted to the central station, e.g., computer, and uploaded automatically. The computer may be programmed to perform an analysis of the pictures to determine if there are any defects or if there is any discoloration that would warrant the cylinder being taken out of service.

Digital cameras may be suspended in various locations so that pictures can be taken of the cylinder from various angles so that the entire cylinder surface can be scanned. The images are then transmitted to the central station, e.g., a computer, either through a wire or via a wireless connection to be processed. Any particular image format is suitable, for example the image could be a bitmap type image (where the color of each pixel is recorded) or it could be any other type of image format.

The computer can be programmed to process the images using any number or combination of image processing techniques ranging from edge detection, filtering, equalization to spectral analysis, principal component analysis, partial least squares, etc. The resulting image can then be further processed to locate and diagnose imperfections such as arc burns, dents, gouges, worn paint, discoloration, etc. The diagnosis may involve a dictionary of images of specific types of defects and it can also include images of cylinders that lack defects.

Once defects are located, the results are displayed to an operator/inspector via a computer screen. The operator/inspector can then decide whether to pass the cylinder for filling or pull the cylinder for maintenance.

Spectral analysis, principal component analysis, or some other advanced image analyzing technique in conjunction with other widely employed image processing techniques such as edge detection, filtering, equalization, could be employed for this purpose. This invention contemplates a wide variety of techniques that exist, are well documented and well established in industry, and any combination of them can be employed in this invention. It is their use in combination with digital photography and the application to a cylinder inspection that is basic to this invention. See, for example, Bharati, M. H., and MacGregor, J. F., "Multivariate Image Analysis for Real-Time Process Monitoring and Control", Industrial and Engineering Chemistry Research, pp. 4715-4724, vol 37, 1998; Champagne, M., and Dudzic, M., "Industrial Use of Multivariate Statistical Analysis for Process Monitoring and Control", Proceedings of the American Control Conference, May 2002; and Champagne, M., and Ivanov, I., "Multigrade Modelling—Paperboard Quality Modeling", Proceedings of the American Control Conference, May 2002; the disclosures of which are incorporated herein by reference.

In other embodiments, this invention may utilize a machine vision method and system for visual inspection of containers. The system may comprise an imaging device configured to acquire image data corresponding to surface defects on containers, an image processor that may be configured to normalize the image data and optionally the system may comprise a light source arranged to illuminate the containers if needed. The image processor may optionally be configured to control adjustment of an exposure control level for the imaging device based upon the normalized image data.

This invention provides a visual inspection system that can be employed, for example, by a machine vision system for inspecting defects in containers using a set of optical arrangements in an inspection process such as commonly occur in automated manufacturing. Under the inspection system, containers can be inspected for compliance with quality metrics such as gouges, dents, burn marks and discoloration, or any other defect optically visible making the container unfit for use.

As indicated above, images of the containers optionally illuminated by a light source may be obtained by an imaging device or camera. The light source may be positioned in any manner that provides the best images of the containers. The light source may be any type of light source which can illuminate the containers.

The camera may be, for example, an analog or CCD (e.g., color) camera such as a line scan camera or a matrix camera, coupled to the vision system for conversion by the machine vision system to a digital representation of the image data, e.g., a pixel representation, corresponding to the containers. The machine vision system can include a display monitor or other equipment for displaying the obtained container image to an operator/inspector for inspection of the containers. After determining the inspection data of the containers under inspection, the machine vision system can provide information about the container's defect position, geometry, size, or other characteristics.

The machine vision system may be automated or semi-automated. For example, the machine vision system may determine if the containers under inspection meet quality control standards with regard to grade or inspection features, etc. These standards can be taught to the vision system by way of producing training templates for examples of containers that meet any established visual inspection quality criteria.

The machine vision system may include an image processing mechanism, a memory, a visual data acquisition system interface, a communication/data/control bus and an equipment interface. The memory may be implemented with, for example, a sufficient quantity of RAM for image processing. The visual data acquisition system interface may include both hardware and software to allow the machine vision system to communicate with a visual data acquisition system which may include a camera. The image processing mechanism may fetch instructions from memory and decode them, which may cause the image processing mechanism to transfer data to or from memory or to work in combination with the equipment interface (for example, to input or output information) or the visual data acquisition system interface (for example, to input image-data from or output instructions to the visual data acquisition system).

In cases where the machine vision system is automated, either fully or partially, the equipment interface may include, for example, software for cooperating with the image processing mechanism or other inspection tools used in such container inspection to determine if a container satisfies inspection criteria. It is within the scope of this invention for the machine vision system to be operated to manually inspect the containers or to be operated in an automated fashion, either in full or in part, to inspect containers.

The processing performed by the image processing mechanisms and the machine vision system may be performed at the central station by a general purpose computer alone or in connection with a specialized image processing computer. Such processing may be performed by a single platform or by a distributed processing platform. In addition, such processing and functionality can be implemented in the form of a special purpose hardware or in the form of software being run by a general purpose computer or any combination of both. Any data handled in such processing or created as a result of such processing can be stored in any memory as is conventional in the art. By way of example, such data may be stored in a temporary memory, such as in the RAM of a given computer system or subsystem. In addition, or in the alternative, such data may be stored in longer term storage devices, for example, magnetic disks, rewritable optical disks, and so on. For purposes herein, a computer-readable media may comprise any form of data storage mechanism, including such existing memory technologies as well as hardware or circuit representations of such structures and of such data.

Machine vision systems that may be useful in carrying out this invention are disclosed, for example, in U.S. Pat. No. 5,812,693 and U.S. Pat. No. 6,531,707 B1, the disclosures of which are incorporated herein by reference. Other optical inspection techniques that may be useful in carrying out this invention are disclosed, for example, in U.S. Pat. No. 5,095,204, U.S. Pat. No. 6,748,104 B1, U.S. Patent Application Publication 2003/0012435 A1, and U.S. Patent Application Publication 2004/0197012 A1.

For the acoustic or sound analysis inspection of containers, this invention relates to a system for recording, displaying and analyzing container sounds to facilitate the inspection of various container defects. The system may include one or more transducers, such as microphones, that may be placed at preselected sites around the container. The microphones detect the sound or vibration of the container at these sites. The system may also include signal processing circuitry for conditioning and converting analog signals generated by the microphones into digital data. Additionally, the system may include a central station, e.g., a computer station, coupled to the signal processing and digitizing circuitry. The computer station may include a processor, input/output circuitry, a data storage device, at least one input device, such as a keyboard or a mouse, and a graphical user interface. The system may further include a printer. Executing on the computer station may be an application program that collects and organizes the data for display on the graphical user interface and/or for printing.

More specifically, one or more transducers or microphones are preferably utilized to obtain sound information from the containers. In response to the container sound, each microphone generates analog signals that are conditioned and digitized by the signal processing circuitry and stored by the computer station at the data storage device. This application program organizes the received data from all sites for simultaneous display on the graphical user interface and/or printing in multiple time scales, such that all of the information may be reviewed concurrently by an operator/inspector. This application program may also display the data in frequency versus time format. In addition, by comparing the displayed or printed combinational data with predefined criteria or guidelines, an accurate inspection may be achieved.

Another application program for progressing an inspection may also be included. This application program may be a data analysis program, such as a defect module or a statistical analysis module using multiple logistic regression models, that interoperates with a database of pre-classified defect sounds. Specifically, the database preferably includes multiple data sets for normal container sounds and container sounds associated with specific defects such as defects with the structural integrity of the container and the accumulation of liquids in the container. The data base may be used to train a person or to perform a statistical classification. The defect module analyzes various quantities computed from the container sounds in view of the database and, if a match of sufficient reliability is found, presents a preliminary assessment and corresponding probability of the defect.

The acoustic or sound analysis inspection preferably may be conducted according to the conventional dead ring test. One or more microphones would be mounted around the testing area. The cylinder would be struck either by the technician or by a machine designed specifically to deliver a consistent impact. Signals from the microphone(s) would be recorded by a computer and stored as waveforms. These waveforms would then be analyzed using spectral, Fourier, or wavelet analysis in conjunction with acoustical filtering techniques and statistical tools to determine if there were any irregularities that would warrant taking the cylinder out of service. This test would also be able to detect the presence of liquids in the cylinder, a task that is difficult for a human being to perform consistently.

The acoustic or sound analysis inspection may include an impact machine that can strike the cylinder in a controlled manner. The machine would propel a metal object towards the cylinder at a particular speed. The shape and speed of the object is pre-determined to replicate the impact that would be delivered by an operator/inspector striking the cylinder with a hammer. Once the cylinder is struck the object recoils so that the sound can resonate. The key is that the machine will strike the cylinder in the same manner every time.

A microphone suspended in the station will pick up the sound and transmit it to the computer as a waveform. Again, the signal can be transmitted over a wire or can be transmitted wirelessly. The computer is programmed to process the signal to determine whether or not the cylinder has a defect. The sound signal can be filtered and then decomposed, preferably using a Fourier transform but could use an alternative method such as a wavelet transform. The decomposed signal is then compared to a database of sounds recorded when various cylinders known to be healthy and damaged were struck. Depending on how the sound signal compares to the database the cylinder is diagnosed as belonging to the healthy or unhealthy category. If desired the computer may be programmed to further categorize the cylinder as to the type of defect it has (for example, if there is water inside of the cylinder).

The diagnostic information from the sound analysis is sent to the display to be communicated to the operator/inspector who can then determine the best course of action to take. Once defects are located, the results are displayed to an operator/inspector via a computer screen. The operator/inspector can then decide whether to pass the cylinder for filling or pull the cylinder for maintenance.

Other acoustic or sound analysis techniques that may be useful in carrying out this invention are disclosed, for example, in U.S. Pat. No. 6,790,183 and U.S. Pat. No. 6,773,398.

For the odor analysis inspection of containers, chemical sensors such as an olfactometer or an electronic nose, e.g., AromaScan™ electronic nose, can be used for the purpose of analyzing the contents of containers, e.g., gases released from containers. Other sensors performing the same function may be used in this invention. The AromaScan™ electronic nose uses conducting polymer sensor arrays to mimic the human olfactory system in the classification, discrimination and recognition of chemical patterns occurring in odor samples. An electronic nose works by measuring the changes in electrical resistance of the sensors when exposed to an odor. The AromaScan™ electronic nose, for example, has 32 different sensors in its array, each of which will in general exhibit a specific change in electrical resistance when exposed to air containing an odor. The selective interaction of odors with the sensors produces a pattern of resistance changes for each odor. If an odor is composed of many chemicals, the pattern will be the result of their combined interactions with all of the sensors in the array.

The electronic nose can be connected to the central station, e.g., a computer or any other suitable electronic device, either through a wire or via a wireless connection. The electronic nose has a sensor output signal that is transmitted to the computer. The computer may contain a memory having a database which stores information obtained as a result of extensive container testing and analysis to identify expected output in the form of a unique or repetitive pattern for the electronic nose product for various gases. The computer can also include software to permit the computer to receive the output data from the electronic nose and, utilizing the information from the database, make appropriate comparisons and generate an identification of the gas. The identification may be presented to the operator/inspector on the computer screen or may be provided to a printer for hard copy output.

The odor analysis inspection preferably may be carried out according to the sniff test using chemical sensors that would act as a "synthetic nose". Readings from the sensors could determine if there were any unusual scents in the gas coming from the cylinder. This would have the benefits of being more consistent than a filling station technician, more sensitive, and able to pick up compounds that ordinarily don't have an odor.

Other odor analysis techniques that may be useful in carrying out this invention are disclosed, for example, in U.S. Pat. No. 6,411,905 B1 and U.S. Pat. No. 6,620,109 B2.

The odor analysis inspection is an optional embodiment of this invention that involves placing a chemical sensor near the cylinder valve. The operator/inspector would open the cylinder valve by a small amount and allow some of the gas to vent and hit the chemical sensor. The chemical sensor would then send the signal to the central station, e.g., computer, in the same manner the camera(s) and microphone(s) send their information to the computer. The computer would be programmed to interpret the data received from the chemical analysis. It would compare the analysis to a dictionary of potentially dangerous chemicals. In this manner the sensor/computer pair acts like a synthetic nose; however, it has the advantage of being able to detect chemicals that do not necessarily have an odor that can be picked up by a human operator/inspector. The results again are sent to the display where an operator/inspector can read the information and determine the appropriate course of action to take with the cylinder.

The order of the inspection tests is not necessarily important, they could even be performed simultaneously; however, in order to guarantee that the cylinder is thoroughly tested, it is best to provide a standard procedure for an operator/inspector to follow where each step in the test is specifically dictated.

This invention relates to a method for carrying out standardized pre-fill testing of industrial gas cylinders. It comprises three parts, each fulfilling a different task ordinarily carried out manually. One part carries out the visual inspection task, another carries out the dead ring test, and another carries out the sniff test. All are related in that they use a central station, e.g., computer, to evaluate the images, sounds, and smells collected by modern sensors, for example, digital cameras, microphones, and chemical sensors.

The method of this invention automates steps of a container inspection process as described herein. The method will provide high reliability that the cylinders are structurally fit to be filled with a pressurized gas. In conducting a cylinder inspection, the method of this invention can provide the following: verify that the cylinder is of a type that meets regulatory body specifications (i.e. the markings must indicate that the cylinder is an approved container);

verify that the cylinder ownership markings are among those approved by company policy;

check the service pressure stamp on the cylinder to verify that the cylinder is safe to fill to the desired pressure;

visually inspect the cylinder for signs of surface damage such as arc burns, torch burns, dents, gouges, bulges, rust, corrosion, pitting, loose collars, mechanical defects, or other damage;

inspect aluminum cylinders for evidence of high temperature exposure detected by heat indicators;

inspect cylinder retest dates to ensure that the cylinder is in compliance with re-qualification requirements;

inspect the exterior of the cylinder for poor external appearance; inspect the valve for signs of damage or contamination; and check for the presence of liquid, cracks in the cylinder wall or the presence of unwanted gases.

As indicated above, the method of this invention obtains image data corresponding to the cylinder using an imaging device configured to transmit the image data to a central station, transmitting a signal including image data to the central station by an electronic circuit in communication between the imaging device and the central station, and processing the image data to detect defects in the container. The imaging device can provide the following:

ensure the cylinder projects a quality appearance;

check the threads of the cylinder collar for wear that would prevent a cap from being tightly secured to the collar;

check the cylinder for surface contamination; and inspect for defects or damage to the external surface; defects to be identified include: dents, cuts, gouges, rusting, pitting, bulges, arc burns, torch burns, fire damage, or an uneven bottom surface; certain cuts, dents, and gouges.

The imaging device of this invention can also be used for inspection of cylinder surface appearance. For example, cylinders should be inspected to ensure that the surface appearance is good. This is done to both ensure customer satisfaction and prevent excessive levels of paint from hiding surface damage that could be caught through visual inspection.

The sound detecting device of this invention can be used for inspection of cylinder structural integrity. Acoustic data generated is similar to that generated by the conventional dead ring test, for which a description follows. For large cylinders, the cylinder is positioned upright. Small cylinders are suspended by the valve. The cylinder is located such that the walls are not touching anything. Any tubing or fishnet protectants are removed from the cylinder. The side of the cylinder is tapped with a ½ pound ball peen hammer or equivalent. A healthy cylinder will make a clear, bell-like tone. If the cylinder does not make such a tone, then it is to be removed from service.

The odor detecting device of this invention can be used for inspection of the cylinder contents. Odor data generated is similar to that generated by the conventional odor test, for which a description follows. The operator/inspector stands at about arms length from the cylinder and the cylinder valve is to be positioned so that it points approximately 90 degrees away from the operator/inspector's face. The valve is slowly opened to discharge a small amount of gas. If the cylinder does not have enough residual gas to allow this discharge, then the cylinder can be filled slightly with an approved gas prior to the odor check. The operator/inspector uses a cupped hand to fan the gas towards his nose. The gas is smelled for unusual odors and then the valve is closed. If an unusual odor is detected then the wall of the cylinder is to be marked accordingly and the cylinder removed from service.

The central station, e.g., computer, can be programmed to process the data transmitted from the imaging device, sound detecting device and odor detecting device. The central station can also be configured to use calibration data from other similar inspections in conjunction with the information received from the imaging device, sound detecting device and odor detecting device in determining irregularities of the container. The central station may further be configured to update the calibration data based on the data received from the imaging device, sound detecting device and odor detecting device. In one embodiment, the central station may comprise a receiver configured to receive the data transmitted from the imaging device, sound detecting device and odor detecting device, a network interface communicatively coupled to a communication network, a transmitter configured to transmit the data received from the imaging device, sound detecting device and odor detecting device through the network interface, and a data processing device communicatively coupled to the communication network, the data processing device configured to receive the data transmitted by the central station.

The apparatus and method of this invention should be capable of handling a range of cylinder sizes from 4 to 5 foot tall cylinders to 1 foot tall cylinders. This can be accomplished by providing a means of suspending the smaller cylinders at the correct elevation or by allowing the sensors to be raised and lowered.

The apparatus or system of this invention may be arranged in several different ways so long as the desired inspection information is generated. Illustrative of such arrangements are as follows:

rather than using several digital cameras, it would be possible to use a single camera and place the cylinder on a turntable that would slowly rotate the cylinder while the digital camera took several pictures of the cylinder as it rotates;

rather than using several digital cameras it would be possible to use one camera and provide a means of revolving the camera around the cylinder while the camera took snapshots of the cylinder surface at regular intervals; this could involve a machine that would move the camera or it could involve the operator/inspector himself taking pictures at specified angles around the cylinder and at a specified distance from the cylinder; the machine that strikes the cylinder to produce the sound for the acoustic test could be replaced with a pendulum where a metal object swings into the side of the cylinder; the pendulum, if drawn a specified distance from the cylinder will always strike the cylinder with a uniform force; alternately an operator/inspector could strike the cylinder with a hammer the same way the dead-ring test is usually administered and the microphone and computer be used to replace the subjective judgment of the operator/inspector interpreting the sound produced; and the odor or chemical sensor could be eliminated altogether and the operator/inspector could be required to perform the sniff test as usual without the assistance of a computer.

It would also be possible to design the inspection apparatus to be portable so that instead of the cylinder being brought to the inspection apparatus it would be possible for the inspection apparatus to be moved. This could be an advantage when analyzing a large number of cylinders (such as in a bank). The inspection apparatus could actually be built into a cylinder rack or a cylinder filling station for convenience with a conveyor used to move the digital camera, striking machine, microphone and optionally chemical sensor along the rack.

More functionality could be built into the central station. Rather than simply display the information to the operator/inspector, the computer could be programmed to take action based on the results. For example, the computer could be hooked up to a machine that would label the cylinder as defective or not (adhesive label or colored mark). This could be something as elaborate as the machine being designed to be able to physically move a questionable cylinder to a quarantine area via a conveyor or other means.

Various modifications and variations of this invention will be obvious to a worker skilled in the art and it is to be understood that such modifications and variations are to be included within the purview of this application and the spirit and scope of the claims.

The invention claimed is:

1. An integrated apparatus for inspection of a container adapted to hold a pressurized gas, the integrated apparatus comprising (i) an imaging device configured to obtain image data corresponding to the container and to transmit the image data to a central station, (ii) an electronic circuit in communication between the imaging device and the central station for transmitting a signal, the signal including image data, to the central station, (iii) a sound detecting device configured to obtain acoustic data corresponding to the container and to transmit the acoustic data to the central station, (iv) an electronic circuit in communication between the sound detecting device and the central station for transmitting a signal, the signal including acoustic data, to the central station, (v) optionally an odor detecting device configured to obtain odor data corresponding to the container contents and to transmit the odor data to the central station, (vi) optionally an electronic circuit in communication between the odor detecting device and the central station for transmitting a signal, the signal including odor data, to the central station, and (vii) the central station comprising a data processing device configured to process data, a receiver configured to receive data transmitted from the imaging device, sound detecting device and odor detecting device, and a transmitter configured to transmit signals received by the receiver or data processed by the data processing device to an external communication network through an external network interface.

2. The apparatus of claim 1 wherein the signal is wired or wireless.

3. The apparatus of claim 1 wherein the imaging device comprises one or more cameras.

4. The apparatus of claim 1 wherein the sound detecting device comprises one or more microphones.

5. The apparatus of claim 1 wherein the odor detecting device comprises one or more chemical sensors.

6. The apparatus of claim 1 wherein the central station comprises a computer.

7. The apparatus of claim 6 wherein the computer is programmed to process the data transmitted from the imaging device, sound detecting device and odor detecting device.

8. The apparatus of claim 1 wherein the central station is configured to use calibration data from other similar inspections in conjunction with the data received from the imaging device, sound detecting device and odor detecting device in determining irregularities of the container.

9. The apparatus of claim 8 wherein the central station is configured to update the calibration data based on the data received from the imaging device, sound detecting device and odor detecting device.

10. An integrated inspection method of a container adapted to hold pressurized gas, the method comprising (i) positioning the container for inspection, (ii) obtaining image data corresponding to the container using an imaging device configured to transmit the image data to a central station, (iii) transmitting a signal including image data to the central station by an electronic circuit in communication between the imaging device and the central station, (iv) processing the image data to detect defects in the container, (v) obtaining acoustic data corresponding to the container using a sound detecting device configured to transmit the acoustic data to the central station, (vi) transmitting a signal including acoustic data to the central station by an electronic circuit in communication between the sound detecting device and the central station, (vii) processing the acoustic data to detect defects in the container and/or the presence of liquids in the container, (viii) optionally obtaining odor data corresponding to the container contents using an odor detecting device configured to transmit the odor data to the central station, (ix) optionally transmitting a signal including odor data to the central station by an electronic circuit in communication between the odor detecting device and the central station, and (x) optionally processing the odor data to identify the container contents; wherein said central station comprises a data processing device configured to process data, a receiver configured to receive data transmitted from the imaging device, sound detecting device and odor detecting device, and a transmitter configured to transmit signals received by the receiver or data processed by the data processing device to an external communication network through an external network interface.

11. The method of claim 10 wherein the signal is wired or wireless.

12. The method of claim 10 wherein the imaging device comprises one or more cameras.

13. The method of claim 10 wherein the sound detecting device comprises one or more microphones.

14. The method of claim 10 wherein the odor detecting device comprises one or more chemical sensors.

15. The method of claim 10 wherein the central station comprises a computer.

16. The apparatus of claim 15 wherein the computer is programmed to process the data transmitted from the imaging device, sound detecting device and odor detecting device.

17. The apparatus of claim 10 wherein the central station is configured to use calibration data from other similar inspections in conjunction with the data received from the imaging device, sound detecting device and odor detecting device in determining irregularities of the container.

18. The apparatus of claim 17 wherein the central station is configured to update the calibration data based on the data received from the imaging device, sound detecting device and odor detecting device.

* * * * *